United States Patent
Wheeler et al.

(10) Patent No.: US 11,278,715 B2
(45) Date of Patent: Mar. 22, 2022

(54) LEAD ASSEMBLY FOR NETWORKED IMPLANTS

(71) Applicant: THE CHARLES STARK DRAPER LABORATORY, INC., Cambridge, MA (US)

(72) Inventors: Jesse J. Wheeler, Revere, MA (US); John Lachapelle, Princeton, MA (US); Caroline K. Bjune, Arlington, MA (US); Philip D. Parks, II, Wayland, MA (US); Carlos A. Segura, Ipswich, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 452 days.

(21) Appl. No.: 15/897,014

(22) Filed: Feb. 14, 2018

(65) Prior Publication Data

US 2018/0229039 A1 Aug. 16, 2018

Related U.S. Application Data

(60) Provisional application No. 62/459,001, filed on Feb. 14, 2017, provisional application No. 62/458,998, filed on Feb. 14, 2017.

(51) Int. Cl.
*A61N 1/05* (2006.01)
*A61N 1/36* (2006.01)
(Continued)

(52) U.S. Cl.
CPC .................. *A61N 1/05* (2013.01); *A61B 5/24* (2021.01); *A61B 5/296* (2021.01); *A61B 5/316* (2021.01);
(Continued)

(58) Field of Classification Search
CPC .......... A61N 1/05; A61N 1/36; A61N 1/3606; A61N 1/36125; A61N 1/36128;
(Continued)

(56) References Cited

U.S. PATENT DOCUMENTS 6,141,588 A 10/2000 Cox et al.
7,006,859 B1 2/2006 Osorio et al.
(Continued)

FOREIGN PATENT DOCUMENTS

WO 03033070 A1 4/2003

OTHER PUBLICATIONS

International Search Report and Written Opinion for application No. PCT/US2018/018244 dated Apr. 26, 2018.
(Continued)

*Primary Examiner* — Tammie K Marlen
(74) *Attorney, Agent, or Firm* — Lando & Anastasi, LLP

(57) ABSTRACT

A lead assembly for networked implants may contain a controller, an implantable tissue contact system connected to the controller and including a plurality of leads, and a breakout connector connected to each of the plurality of leads, and further connected to a shared communication path. A physiological interface system may contain a controller and an implantable tissue contact system. Methods of treating a subject and monitoring a subject include transmitting signals between a controller and an implantable tissue contact system.

20 Claims, 2 Drawing Sheets

(51) Int. Cl.
*A61B 5/00* (2006.01)
*A61B 5/24* (2021.01)
*A61B 5/296* (2021.01)
*A61B 5/316* (2021.01)
*A61N 1/365* (2006.01)
*A61N 1/372* (2006.01)
*A61N 1/04* (2006.01)
*A61B 5/30* (2021.01)

(52) U.S. Cl.
CPC .......... *A61B 5/6847* (2013.01); *A61B 5/6877* (2013.01); *A61N 1/36* (2013.01); *A61N 1/365* (2013.01); *A61N 1/3606* (2013.01); *A61N 1/36125* (2013.01); *A61N 1/36128* (2013.01); *A61N 1/37211* (2013.01); *A61B 5/30* (2021.01); *A61B 2562/028* (2013.01); *A61B 2562/04* (2013.01); *A61B 2562/125* (2013.01); *A61N 1/0404* (2013.01); *A61N 1/0502* (2013.01); *A61N 1/0504* (2013.01); *A61N 1/36003* (2013.01); *A61N 1/36062* (2017.08); *A61N 1/36114* (2013.01)

(58) Field of Classification Search
CPC .. A61N 1/365; A61N 1/3721; A61N 1/36062; A61N 1/0404; A61N 1/0502; A61N 1/0504; A61N 1/36003; A61N 1/36114; A61N 1/37211; A61B 5/04001; A61B 5/04012; A61B 5/0492; A61B 5/6847; A61B 5/6877; A61B 5/04004; A61B 2562/04; A61B 2562/125; A61B 2562/028; A61B 5/296; A61B 5/24; A61B 5/316; A61B 5/30
See application file for complete search history.

(56) References Cited

U.S. PATENT DOCUMENTS

| | | |
|---|---|---|
| 2008/0154328 A1 | 6/2008 | Thompson et al. |
| 2009/0118804 A1 | 5/2009 | Moffitt et al. |
| 2012/0277834 A1 | 11/2012 | Mercanzini et al. |
| 2013/0289683 A1 | 10/2013 | Parker et al. |
| 2014/0343621 A1 | 11/2014 | Decre et al. |
| 2016/0015979 A1 | 1/2016 | McLaughlin et al. |
| 2016/0074655 A1 | 3/2016 | Mercanzini et al. |
| 2016/0270679 A1 | 9/2016 | Mahon et al. |
| 2016/0331973 A1 | 11/2016 | Wheeler et al. |
| 2017/0225447 A1* | 8/2017 | Varadan ................. B41F 17/38 |

OTHER PUBLICATIONS

Invitation to Pay Additional Fees and Partial International Search Report for application No. PCT/US2018/018243 dated Apr. 25, 2018.

International Search Report and Written Opinion for application No. PCT/US2018/018243 dated Jun. 19, 2018.

* cited by examiner

LEAD ASSEMBLY FOR NETWORKED IMPLANTS

CROSS-REFERENCE TO RELATED APPLICATIONS

This application claims priority under 35 U.S.C. § 119(e) to U.S. Provisional Application Ser. No. 62/459,001 titled "LEAD ASSEMBLY FOR NETWORKED IMPLANTS," filed Feb. 14, 2017, and U.S. Provisional Application No. 62/458,998 titled "ELECTRODE ARRAY FOR SURFACE AND INTRATISSUE RECORDING AND STIMULATION," filed Feb. 14, 2017, which are incorporated herein by reference in their entireties for all purposes.

FIELD OF TECHNOLOGY

The disclosure relates to implantable medical devices in general, and networked implantable medical devices in particular.

SUMMARY

Aspects and embodiments are directed to a lead assembly for networked implants. The assembly may comprise an implantable tissue contact system and a controller. The implantable tissue contact system may comprise a plurality of leads and a breakout connector connected to each of the plurality of leads and a shared communication path. The controller may be connected to the breakout connector though the shared communication path.

In some embodiments, at least one of the breakout connector and the controller are implantable in a target tissue.

The implantable tissue contact system may be at least one of a recording, stimulation, wireless data receiving, and energy harvesting system. Thus, the implantable tissue contact system may be configured to do at least one of receive and transmit signals to the target tissue. The signals may be at least one of electrical, chemical, and optical signals.

The shared communication path may be configured to transmit at least one of power and data between the plurality of leads and the controller. The shared communication path may be a passive connection, such that the breakout connector is configured to splice at least one of power and data from the shared communication path to the plurality of leads. In other embodiments, the breakout connector may be an active electronic module configured to selectively transmit at least one of power and data between each of the plurality of leads and the controller.

In some aspects, a physiological interface system comprises a controller and an implantable tissue contact system. The controller may comprise an energy source. The controller may be constructed and arranged to do at least one of provide and receive at least one shared signal. The implantable tissue contact system may be connected to the controller. The implantable tissue contact system may comprise a plurality of leads constructed and arranged to do at least one of transmit and receive the at least one shared signal and a plurality of tissue contacts associated with the plurality of leads. The plurality of tissue contacts may be constructed and arranged to enable at least one of reception and delivery of signals to at least one predetermined treatment site. The implantable tissue contact system may comprise an antenna connectable to the controller and the plurality of leads. In some embodiments, the at least one shared signal is wireless.

The implantable tissue contact system may be configured to do at least one of record signals, stimulate, receive wireless data, and harvest energy from the at least one predetermined treatment site. The signals may comprise at least one of an electrical, chemical, and optical signal.

The plurality of tissue contacts may be constructed and arranged to enable at least one of reception and delivery of signals to more than one predetermined treatment site. In some embodiments, each predetermined treatment site is remote from other predetermined treatment sites.

The plurality of tissue contacts may be constructed and arranged to selectively enable at least one of reception and delivery of signals to each predetermined treatment site.

In some aspects, a method of treating a subject comprises generating a first output signal from a controller, transmitting the first output signal from the controller to a tissue contact system having a plurality of leads and a breakout connector, generating a shared output signal based at least partially on the first output signal from the controller, transmitting the shared output signal to the breakout connector, generating a plurality of selective output signals based at least partially on the first output signal from the breakout connector, and transmitting the plurality of selective output signals to the plurality of leads in contact with a tissue of a predetermined treatment site.

In some embodiments, each of the selective output signals is discrete from other selective output signals.

In some embodiments, at least one of the first output signal, the shared output signal and the plurality of selective output signals may comprise at least one of an electrical, chemical, or optical signal.

In some aspects, a method of monitoring a subject comprises receiving a plurality of selective input signals from a predetermined treatment site through a plurality of leads, transmitting the plurality of selective input signals to a breakout connector, generating a shared input signal based at least partially on the plurality of selective input signals from the plurality of leads, transmitting the shared input signal to a controller, and interpreting the first input signal.

In some embodiments, each of the selective input signals is discrete from other selective input signals.

In some embodiments, at least one of the shared input signal and the plurality of selective input signals comprises at least one of an electrical, chemical, and optical signal.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
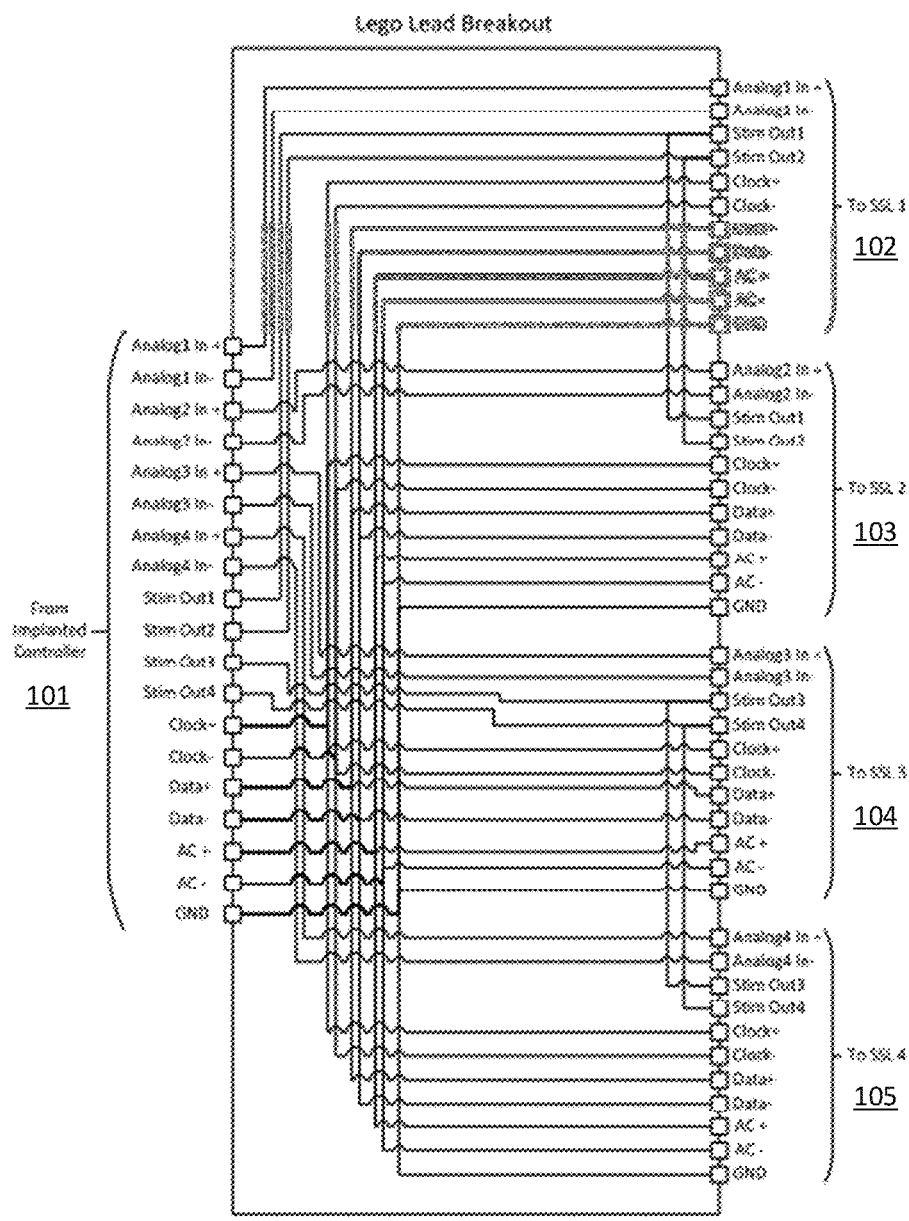
FIG. 1 is a signal diagram of a system according to an exemplary embodiment.

Medical devices can be implanted within the human body. These devices may sense, analyze, and communicate data to deliver a therapeutic effect to a patient. Implantable devices may additionally or alternatively sense, analyze, and communicate data to monitor and/or record information from the patient. A plurality of implanted medical devices may be networked, allowing them to communicate with each other at a distance and without any action on the part of the user. Each device may sense a physiological parameter, and the networked implants and leads may perform such therapeutic tasks as drug delivery, executable actions, and sensory stimuli delivery or suppression within the patient's body. The networked leads may receive and transmit electrical, chemical, or optical signals. The networked leads may receive and transmit data to provide or monitor localized electrical, chemical, or optical signals.

A controller may communicate with each device within the body. The controller may be implanted, implantable, or external. Conventionally, controllers may not be equipped to distinguish between devices. Thus, controllers may send every signal to each implanted device, and not distinguish between devices.

Implanted sensors and actuators for medical applications may reduce the invasiveness and the number of medical procedures a patient may undergo. Implanted devices may deliver drugs, stimulate or suppress sensory stimuli, or internally monitor the health of a patient. A network of medical implants may include a plurality of in vivo medical devices, a communication path between at least two of the devices, a controller to control the behavior of the devices, and a communication path between the controller and at least one of the devices.

The networked implants may be sensors in the human body that collect various physiological changes in order to monitor the patient's health status regardless of their location. The information may be transmitted to a controller, which may control at least one of the implants or a lead within the body. Information may also be transmitted wirelessly to an external processing unit.

In some embodiments, the networked implants may be used for continuous monitoring and logging vital parameters of patients. For example, vital parameters of a patient with a chronic disease may be continuously monitored. In this way, the network may, for example, alert a hospital even before a patient has a heart attack, by measuring changes in his vital signs. A network may, for example, auto-inject insulin through a pump of a diabetic patient as soon as the patient's insulin level reaches a threshold level. In some embodiments, a network may stimulate a nerve of an Alzheimer's patient. The network may also be used for regulating blood pressure by stimulating the vagus nerve in response to a measured blood pressure value in a different area of the body. In some embodiments, the network may be used for cardiac pacing, or for spinal stimulation.

An implant network may comprise a controller. The controller may be implantable or external. The controller may communicate with a number of implantable devices. In some embodiments, the controller may communicate with at least one satellite or implantable system. The at least one satellite or implantable system may comprise a lead. In some embodiments, the controller may communicate with a plurality of leads.

A lead is an tissue connection consisting of a length of material that comes from a device. The lead may be an electrical, chemical, or optical lead. The leads may be used to transmit information, transfer power, and/or probe circuits. In some embodiments, a lead may receive an information signal from a controller and, responsive to the signal, perform a task, such as stimulating a nerve or muscle. In some embodiments, leads may be capable of transmitting at least one type of stimulation or signal. In some embodiments, satellite systems may comprise more than one lead, each lead capable of transmitting a discrete type of stimulation or signal.

The controller may be configured to receive control signals and send control signals. For example, the controller may be configured to receive input control signals and send output control signals. The input control signals may be sent from a device that generates at least one signal. The device may be a medical-related device that supplies input signals to the controller. The device may comprise a pulse generator. The device may also comprise an energy source to energize the pulse generator. The device may comprise a data processor or storage. In some embodiments, the controller may be constructed and arranged to derive its energy from the energy source of the device. In one embodiment, the energy source of the implantable device is a battery.

The tissue contact system, sometimes referred to herein as the "device," may be an implantable device. The device may be at least partially implantable into a subject, such as a human or other mammal. For example, the device may be implantable in the chest region of a subject. The device may be surgically put in place, and may also be surgically removable. At least one of the input control signal and the output control signal may be in the form of a waveform, such as a stimulus waveform.

The controller may provide at least one of power harvesting, electrical stimulus generation, optical stimulus generation, pulse generation, pulse shaping, pulse pass-through, multiplexing, charge balance shaping, and impedance measurement or sensing to measure therapy effectiveness (for example, charge delivery). The controller may be configured to harvest power from the implantable device to energize the controller. The implantable device may provide at least a portion of the power to the controller to energize the controller. In certain embodiments, the implantable device may provide the power to the controller to energize the controller.

The controller may be configured to send at least one electrical signal to at least one tissue contact at a distal end of the lead body. The controller may be configured to send at least one electrical signal to each of the tissue contacts at a distal end of a sensory stimulator lead body. The tissue contacts, in this example, may be electrodes. The controller may also be configured to send at least one optical or chemical signal to each of the tissue contacts at a distal end of a lead body.

The controller may also provide closed loop control using input signals from the tissue contacts to modify control and stimulation functions. The controller may send at least one output control signal to at least one tissue contact. The tissue contact may then transmit at least one input signal to the controller. The control unit may then further send at least one output signal to at least one tissue contact, based on the at least one input signal. The controller may also send the at least one output signal to at least one tissue contact based on a control function of the controller.

The controller may also be capable of performing decision making. The controller may be configured to communicate or send signals back to the device, for example, the implantable device. In addition or in the alternative, the controller may be configured, to receive signals from the device. The controller may also be configured to communicate or send signals to the tissue contacts. In addition or in the alternative, the controller may be configured to receive signals from the tissue contacts.

Power to the controller may be harvested from the implantable device. The power may be applied using lead wires between the implantable device and the controller. In certain embodiments, AC-coupled only signals may be used to ensure or reduce damage due to any wire breakage or leakage, or any other event that may cause tissue damage if a DC signal were to be applied. Power may also be provided wirelessly. This may be accomplished using coupled radio-frequency antennas or acoustic transducers.

In certain embodiments the controller may be a bio-compatible by an integrated ultra high density integrated circuit-based device. The controller or device may be enclosed or encapsulated by a material, such as a thin-film hermetic material, that may provide a hermetic seal. The material may be a bio-compatible material. The material may be deposited using a sputtering or atomic layer deposition process. The contacts of the controller or device and the input and output locations may also be composed of bio-compatible materials.

Typically, conventional equipment used in the applications disclosed may comprise an implantable medical device which comprises electronics, battery, processor, and stimulatory circuitry. In some embodiments, an electrode lead is connected to the implanted device, and carries a stimulus pulse to the distal end of the lead, where current may exit the lead through transducer contacts and enters the tissue that it is in contact with.

Parameters that may be sensed or transmitted may include electrical responses, blood pressure, heart rate, temperature, and pressure. Parameters may also include other physiological properties that may be useful in treatment of a subject or in diagnostic testing of a subject.

The lead body may be configured to be connectable to an implantable device. The implantable device may comprise an energy source. The implantable device may be constructed and arranged to provide a signal. The lead may be passive, and may propagate messages.

Each sensory stimulation lead may be connected to the controller by a shared connection path. In some embodiments, a plurality of leads make up a sensory lead system. In conventional systems, the controller is not connected to a shared wire for the combination of output signals, but is instead connected to a plurality of output wires—one for each signal—which are then connected to each lead. Because of this, each lead is connected to a number of wires, and the controller is connected to more than one wire. In some embodiments, wires selectively connect each lead with the controller, such that not every wire connects each lead with the controller. For example, the wires may be selectively spliced to the individual leads from the shared wire.

The implantable tissue contact system may be at least one of a recording, stimulation, wireless data receiving, and energy harvesting system. Thus, the implantable tissue contact system may be configured to do at least one of receive and transmit signals to the target tissue. Generally, the implantable tissue contact system may be capable of both transmitting signals or stimulation from the controller and receiving signals from the plurality of leads. The signals may be at least one of electrical, chemical, and optical signals. In some embodiments, the implantable tissue contact system is capable of processing more than one type of signal. For example, discrete leads may each be capable of processing different types of signals. The signals from discrete leads may be combined in a shared signal to provide a comprehensive stimulation to the target tissue or receive comprehensive information about the conditions of the target tissue.

The signals transmitted between the controller and the implantable device may be consolidated in a shared communication path. The shared communication path may be a passive connection. The signal or stimulation emitted by the controller may be passively spliced such that the signal transmitted to each of the leads is essentially equivalent. In such an embodiment, the shared communication signal may be spliced evenly by a breakout connector.

In other embodiments, the breakout connector may be an active electronic module. The breakout connector may selectively transmit signals between the controller and the plurality of leads. Thus, discrete signals may be transmitted to different leads of the plurality of leads.

In some embodiments, the controller of the system is configured to generate at least one first output signal and to transmit a plurality of output signals to the plurality of tissue contacts. The plurality of output signals may be based at least in part on the at least one first output signal from a control function of the controller. The output signal of the controller may be transmitted to the device, which in turn generates a shared output signal. A breakout connector may splice the shared output signal into the plurality of selective output signals. The plurality of selective output signals may be transmitted by the plurality of leads to a plurality of target tissues. In some embodiments, the controller is further configured to receive at least one signal from the plurality of tissue contacts, and the plurality of output signals is modulated in response to the at least one signal from the plurality of tissue contacts.

In some embodiments, the selective output signals are discrete output signals. The breakout connector may selectively distribute or direct the plurality of selective output signals to the plurality of leads. Each of these signals may comprise at least one of an electrical, chemical, or optical signal. The methods of transmitting signals from the controller to a target tissue may be used to treat a subject. Any number of conditions, as described above, may be treated by the methods disclosed herein. For instance, the target tissue may be a predetermined treatment site.

There may be no limit to the number of signals emitted by the controller, and no limit to the number of signals received by each lead. For example, the number of signals may be more than 10, more than 15, more than 25, or more than 50. In some embodiments, the output wires of the controller may share a common line, and selective individual lines may branch off of the common line to the leads. This may make the system smaller, safer, and less prone to failure than conventional systems having a single hub and not having a shared line.

The signals communicated from the controller to the leads may be analog signals. An analog signal is any continuous signal for which the time varying feature, or variable, of the signal is a representation of some other time varying quantity. It is analogous to another time varying signal. Any information may be conveyed by the analog signal. For example, the signal may be a measured response to changes in physical phenomena, such as temperature, position, concentration, or pressure. The physical variable is converted to an analog signal by a transducer. For example, the signal may be a voltage or current that is said to be an "analog" of the physical variable.

In some embodiments, the signals communicated from the controller to the leads may be digital signals. A digital signal is an electrical signal that is converted into a pattern of bits. Unlike an analog signal, which is a continuous signal that contains time-varying quantities, a digital signal has a discrete value at each sampling point.

The systems and methods disclosed herein may be used to monitor a subject. In particular, the methods may be used to monitor a target tissue or tissue function of a subject. The plurality of leads may receive a plurality of selective input signals from a target tissue. The plurality of selective input signals may be transmitted to the controller for monitoring. The plurality of input signals may be consolidated into a shared signal for the controller by the breakout connector. In some embodiments, the plurality of selective input signals comprise discrete signals. By consolidating the signals into a shared signal for the controller, device complexity may be reduced. The signals may be interpreted by the controller to further generate a responsive output signal. In some embodiments, the controller transmits the signal to an external hub for user analysis.

The breakout system disclosed herein may eliminate the need for extension of leads and/or multiple lead lengths. The breakout system may also reduce and distribute the total connector wire volume or system complexity. The breakout system may also enable a single high density controller as the main hub, eliminating the need for multiple controllers.

In some embodiments, the implantable system may be between about 1 mm and about 10 mm in diameter. For example, the implantable system may be between about 1 mm and about 5 mm in diameter. The implantable system may be about 2 mm in diameter.

The implantable system may be composed of materials having high electrical isolation, and any conductors should be non-corrosive within the body. The implantable system may be secured within the body, and may be flexible. In some embodiments, the implantable system may be implanted surgically within the patient. In some embodiments, the implantable system may be implanted arthroscopically within the patient.

Each breakout connection should exhibit low electrical impedance so that it is not resistant to the electrical current. In contrast, each breakout connection should exhibit high electrical impedance so as not to receive electrical signals from adjacent breakout connections.

In some embodiments, referring to FIG. 1, the lead system may comprise at least four leads 102, 103, 104, 105. The controller 101 may send 11 of its 19 signals to each lead, or satellite. Each signal is associated with a shared wire, such that each lead is connected to the controller by one spliced wire. This is in contrast to conventional systems in which the controller sends all 19 signals to each lead via 19 separate wires. This can cause an unnecessarily high number of wires to be between each lead and the controller.

In some embodiments, the controller selectively sends signals to each lead. For example, the controller 101 selectively sends signals to each lead 102, 103, 104, 105. The controller 101 may still output a total of 19 signals, but may only communicate with a selected lead, for example, one lead. The reduced number of wires from the controller to each lead makes connecting each of the leads to the controller a simpler task. The number of high channel count wires and interconnects needed to connect multiple satellite systems together may also be reduced.

Still referring to FIG. 1, the leads may be connected to the controller by breakout connections. As discussed above, in some embodiments, 11 breakout connections may connect each lead to the controller. The breakout connections may be part of a breakout connector comprising a box or a cable. This may be a mechanical enclosure in which a connector's aggregate connections are separated, or broken out, into individual signal or current carrying wires or cables. In some embodiments, the breakout connector may be constructed and arranged to splice the shared wire to an individual lead.

In some embodiments, this may be accomplished by employing an active electronic module as the breakout connector. In some embodiments, this may be accomplished by using a controller. The controller may enable the availability of a number of implantable devices to deliver the electrical current or signals and be in contact with the target location of a subject. The controller may direct incoming stimulus waveforms from a number of input wires or filaments that are in communication with a device such as an implantable device, to a number of output wires or filaments that deliver electrical current or other signals to a number of tissue contacts. The number of output wires or filaments from the control unit that deliver current to a number of tissue contacts is typically greater than the number of input wires or filaments.

Figure 2:
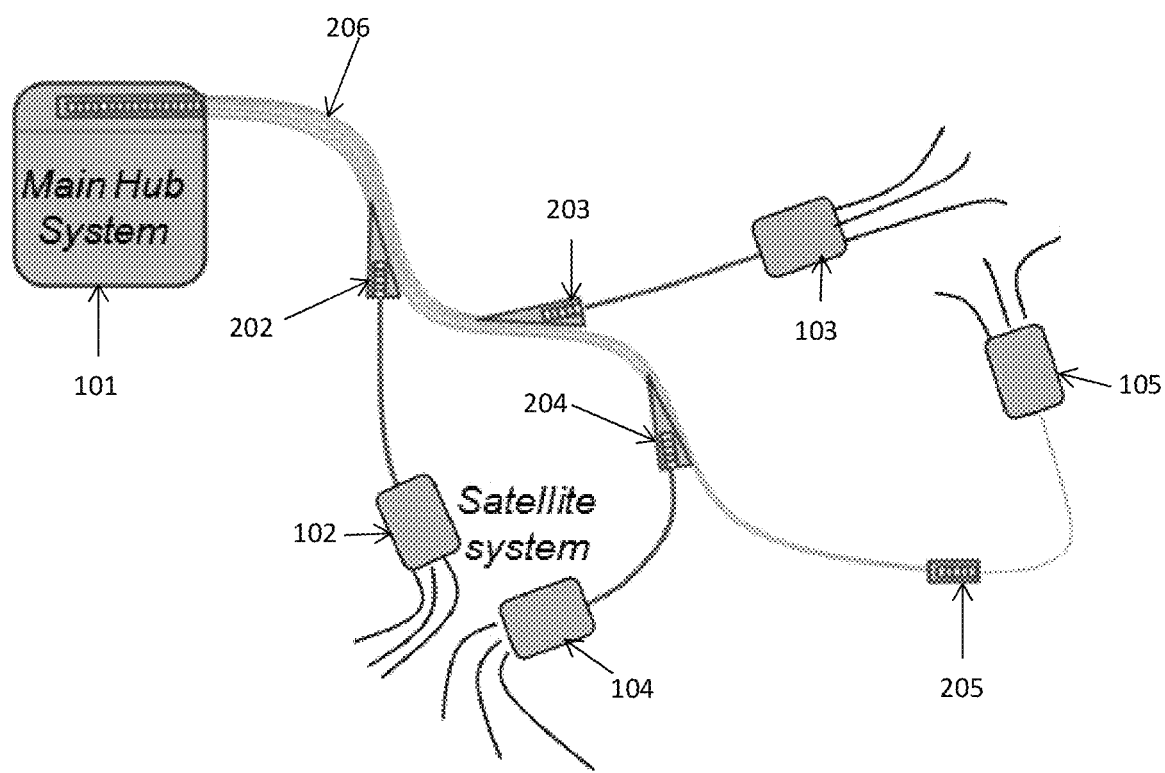
FIG. 2 is a schematic of a system according to an exemplary embodiment.

Turning to FIG. 2, a lead breakout system is shown. The main hub system, or controller, 101 may be in communication with leads 102, 103, 104, 105. Spliced wires 201, carrying signals from controller 101, may be connected to leads 102, 103, 104, 105 through breakout connections 202, 203, 204, 205, respectively. The output wire from the controller may be a shared signal wire, which may comprise all of the output signals. The necessary signals for each sensory stimulation lead may branch off from the shared signal wire at the desired location, such as at the desired sensory stimulation lead. The lead breakout system may be scaled up to higher channel counts by multiplexing the signals down.

Figure 3:
FIG. 3 is a schematic of a system according to an exemplary embodiment.

FIG. 3 shows the shared wire 206 as it is branched out and spliced into selective leads.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A lead assembly for networked implants, comprising:
an implantable tissue contact system comprising a plurality of leads, each lead connected to a plurality of tissue contacts, the plurality of leads being interconnected;
a plurality of breakout connectors, each breakout connector connected to an associated lead of the plurality of leads;
a shared communication path having one shared wire; and
a controller connected to the plurality of breakout connectors through the shared communication path, each of the breakout connectors being an active electronic module configured to selectively transmit at least one of power and data between each of the plurality of leads and the controller.

2. The lead assembly of claim 1, wherein at least one of the plurality of breakout connectors and the controller are implantable in a target tissue.

3. The lead assembly of claim 1, wherein the implantable tissue contact system is at least one of a recording, stimulation, wireless data receiving, and energy harvesting system.

4. The lead assembly of claim 3, wherein the implantable tissue contact system is configured to do at least one of receive and transmit at least one of electrical, chemical, and optical signals to a target tissue.

5. The lead assembly of claim 1, wherein the controller is configured to provide at least one optical shared output signal through the shared communication path and the plurality of breakout connectors are configured to splice the optical shared output signal into a plurality of selective output signals to be transmitted to the plurality of leads.

6. The lead assembly of claim 1, wherein the plurality of leads are configured to receive a plurality of discrete input signals and the plurality of breakout connectors are configured to consolidate the plurality of discrete input signals into an optical shared input signal to be transmitted to the controller through the shared communication path.

7. A physiological interface system comprising:
the lead assembly of claim 1,
wherein the controller comprises an energy source, the controller constructed and arranged to do at least one of provide at least one shared output signal and receive at least one shared input signal;
the plurality of leads being constructed and arranged to do at least one of transmit and receive discrete signals;
the plurality of breakout connectors being configured to at least one of splice the at least one shared output signal into the discrete signals, and consolidate the discrete signals into the at least one shared input signal;
the shared communication path being configured to transmit the at least one shared input signal and shared output signal between the plurality of breakout connectors and the controller; and
the plurality of tissue contacts constructed and arranged to enable at least one of reception and delivery of the discrete signals to at least one predetermined treatment site.

8. The system of claim 7, wherein the controller comprises an antenna wirelessly connectable to an external processing unit.

9. The system of claim 7, wherein the implantable tissue contact system is configured to do at least one of record signals, stimulate, receive wireless data, and harvest energy from the at least one predetermined treatment site.

10. The system of claim 9, wherein the discrete signals comprise at least one of an electrical, chemical, and optical signal.

11. The system of claim 7, wherein the plurality of tissue contacts are constructed and arranged to enable at least one of reception and delivery of the discrete signals to more than one predetermined treatment site.

12. The system of claim 11, wherein each predetermined treatment site is remote from other predetermined treatment sites.

13. The system of claim 12, wherein the plurality of tissue contacts are constructed and arranged to selectively enable at least one of reception and delivery of the discrete signals to each predetermined treatment site.

14. A lead assembly for networked implants, comprising:
a bio-compatible tissue contact system implantable in an internal target tissue, the tissue contact system comprising a plurality of leads and a breakout connector connected to each of the plurality of leads;
a shared communication path having one shared wire; and
a controller connected to the breakout connector through the shared communication path,
the shared communication path being configured to transmit optical shared signals between the implantable tissue contact system and the controller.

15. The lead assembly of claim 14, wherein the controller is implantable in the target tissue.

16. The lead assembly of claim 14, wherein the implantable tissue contact system is at least one of a recording, stimulation, wireless data receiving, and energy harvesting system.

17. The lead assembly of claim 16, wherein the implantable tissue contact system is configured to do at least one of receive and transmit at least one of electrical, chemical, and optical signals to a target tissue.

18. The lead assembly of claim 14, wherein the shared communication path is configured to transmit at least one of power and data between the plurality of leads and the controller.

19. The lead assembly of claim 18, wherein the shared communication path is a passive connection and the breakout connector is configured to splice at least one of power and data from the shared communication path to the plurality of leads.

20. The lead assembly of claim 18, wherein the breakout connector is an active electronic module configured to selectively transmit at least one of power and data between each of the plurality of leads and the controller.

* * * * *